United States Patent
Suzuki et al.

[11] Patent Number: 6,132,751
[45] Date of Patent: *Oct. 17, 2000

[54] O/W EMULSION COMPOSITION FOR EYE DROPS

[75] Inventors: Hidekazu Suzuki; Satoshi Yamazaki; Yoshikazu Naito; Takahiro Wada; Kaei Nagoshi; Noriko Tahira; Reiko Hirata; Touru Oguma; Makoto Maeda, all of Tokyo, Japan

[73] Assignee: Wakamoto Pharmaceutical Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 09/000,150
[22] PCT Filed: Aug. 5, 1996
[86] PCT No.: PCT/JP96/02187
    § 371 Date: Feb. 3, 1998
    § 102(e) Date: Feb. 3, 1998
[87] PCT Pub. No.: WO97/05882
    PCT Pub. Date: Feb. 20, 1997

[30] Foreign Application Priority Data

Aug. 4, 1995  [JP]  Japan .................... 7-218307

[51] Int. Cl.⁷ ................ A61F 2/00; A61F 13/00
[52] U.S. Cl. ............ 424/422; 424/427; 424/428
[58] Field of Search ................. 424/422, 427, 424/428

[56] References Cited

U.S. PATENT DOCUMENTS

| | | | |
|---|---|---|---|
| 4,419,352 | 12/1983 | Cox et al. | 424/248 |
| 4,670,185 | 6/1987 | Fujiwara et al. | 252/311 |
| 4,789,667 | 12/1988 | Makino et al. | 514/161 |

FOREIGN PATENT DOCUMENTS

| | | |
|---|---|---|
| 0 696 452 | 2/1996 | European Pat. Off. |
| 0 700 678 | 3/1996 | European Pat. Off. |
| 89/06964 | 8/1989 | WIPO . |
| 89/09057 | 10/1989 | WIPO . |
| 94/05298 | 3/1994 | WIPO . |
| 95/05161 | 2/1995 | WIPO . |
| 96/40051 | 12/1996 | WIPO . |

*Primary Examiner*—Jose' G. Dees
*Assistant Examiner*—Kathryne E. Shelborne
*Attorney, Agent, or Firm*—Oblon, Spivak, McClelland, Maier & Neustadt, P.C.

[57] ABSTRACT

An O/W emulsion composition for eye drops comprises a drug selected from the group consisting of fluorometholone, clobetasone butyrate and clobetasol propionate; a phospholipid; liquid paraffine; and water. The O/W emulsion composition is excellent in solubility of fluorometholone, clobetasone butyrate and clobetasol propionate in the tear fluid. Therefore, the composition would exhibit an antiinflammatory activity identical to or superior to those achieved by the conventional pharmaceutical preparations, by the administration thereof at a dose lower than those for these known drugs. The composition would also be excellent from the economical standpoint and permit reduction of systemic side effects which would be encountered when the conventional drugs are instilled in the eyes.

21 Claims, 2 Drawing Sheets

\*\* : There was observed a significant difference with respect to the suspension at $p < 0.01$ ( t Test ).

O/W EMULSION COMPOSITION FOR EYE DROPS

TECHNICAL FIELD

The present invention relates to an O/W emulsion composition for eye drops. More specifically, the present invention relates to an O/W emulsion composition for eye drops which comprises a drug selected from the group consisting of fluorometholone, clobetasone butyrate and clobetasol propionate, a phospholipid, liquid paraffin and water and which is excellent in solubility of fluorometholone, clobetasone butyrate and clobetasol propionate in the tear fluid.

BACKGROUND ART

Fluorometholone, clobetasone butyrate and clobetasol propionate used in the present invention are synthetic adrenocortical hormones each exhibiting a strong anti-inflammatory action and, in particular, fluorometholone and clobetasone butyrate are drugs effective for treating inflammatory diseases at external-ocular and anterior-ocular sites. However, these drugs are hardly soluble in water and therefore, it is impossible to dispense these drugs like the usual aqueous eye drops. For this reason, fluorometholone and clobetasone butyrate have been used in ophthalmology in the form of an aqueous suspension prepared by pulverizing crystals of each drug into fine particles and dispersing and suspending the particles in an appropriate amount in an aqueous solution for eye drops, but these aqueous suspensions suffer from problems such that they are bad in feeling when they are applied to the eyes and that the fine particles thereof precipitate and solidify at the bottom of the container thereof, as a result, they are never redispersed uniformly even if the suspension is vigorously shaken. Moreover, solubility of crystal particles of fluorometholone and clobetasone butyrate in the tear fluid is low and therefore, the bioavailability thereof is also low.

In general, drugs hardly soluble in water have been solubilized therein by the use of various kinds of surfactants or other additives having effects similar to those of the surfactants. However, such additives used in commercially available eye drops as medical additives have been limited to those having relatively weak solubilization ability from the viewpoint of safety. Therefore, it is difficult to solubilize drugs hardly soluble in water such as fluorometholone, clobetasone butyrate and clobetasol propionate in an amount effective for preparing pharmaceutical preparations thereof. Under such circumstances, there has been proposed a method in which fluorometholone is included in dimethyl-β-cyclodextrin to thus enhance the solubility thereof in water [Japanese Un-Examined Patent Publication (hereinafter referred to as "J. P. KOKAI") No. Sho 59-130900] and a method in which clobetasone butyrate is included in heptakis(2,6-di-O-methyl)-β-cyclodextrin to thus enhance the solubility thereof in water(J. P. KOKAI No. Sho 61-129115), but such methods have not yet been put into practical use.

On the other hand, there have been disclosed O/W emulsion compositions each of which comprises a drug, an oil, a phospholipid and a surfactant (J. P. KOKAI No. Hei 5-186333 and WO 94/05298) as prior arts concerning vehicles for instilled drugs hardly soluble in water in the eyes.

DISCLOSURE OF THE INVENTION

The present invention has been developed for solving the problems associated with the conventional techniques for solubilizing, in water, drugs hardly soluble in water and therefore, an object of the present invention is to provide a novel composition for eye drops which is excellent in solubility of fluorometholone, clobetasone butyrate and clobetasol propionate in the tear fluid. The inventors of this invention have conducted intensive studies to accomplish the foregoing object, have found out that an O/W emulsion composition which comprises one drug selected from the group consisting of fluorometholone, clobetasone butyrate and clobetasol propionate, a phospholipid, liquid paraffin and water permits the considerable improvement in solubility of fluorometholone, clobetasone butyrate and clobetasol propionate in the tear fluid and thus have completed the present invention.

More specifically, the present invention relates to an O/W emulsion composition which comprises one drug selected from the group consisting of fluorometholone, clobetasone butyrate and clobetasol propionate, a phospholipid, liquid paraffin and water. In the composition of the present invention, solubility of fluorometholone, clobetasone butyrate and clobetasol propionate in the tear fluid can be controlled by appropriately adjusting the mixing ratio of the components of the composition. The fluorometholone, clobetasone butyrate or clobetasol propionate-containing O/W emulsion composition according to the present invention can effectively be used, in the form of an eye drop, for the treatments of various ocular diseases, for instance, inflammatory diseases of external- and anterior-ocular sites such as blepharitis, conjunctivitis, keratitis, scleritis, episcleritis, iritis, iridocyclitis and uveitis as well as inflammatory diseases developed after ocular operations.

BEST MODE FOR CARRYING OUT THE INVENTION

The present invention will hereinafter be explained in more detail.

The O/W emulsion composition for eye drops according to the present invention preferably comprises the following components A to D.

A. one drug selected from the group consisting of fluorometholone, clobetasone butyrate and clobetasol propionate in an amount ranging from 0.001 to 0.05% (w/v);

B. a phospholipid in an amount ranging from 5 to 240 parts by weight per one part by weight of the component A;

C. liquid paraffin in an amount ranging from 0.5 to 80 parts by weight per one part by weight of the component B and at a concentration in the O/W emulsion of not more than 25% (w/v); and D. an appropriate amount of water.

The O/W emulsion composition for eye drops according to a first embodiment of the present invention preferably comprises the following components A to D.

A. fluorometholone in an amount ranging from 0.001 to 0.05% (w/v) and preferably 0.005 to 0.05% (w/v);

B. a phospholipid in an amount ranging from 10 to 240 parts by weight and preferably 20 to 100 parts by weight per one part by weight of the component A;

C. liquid paraffin in an amount ranging from 0.5 to 20 parts by weight and preferably 3 to 20 parts by weight per one part by weight of the component B and at a concentration in the O/W emulsion of not more than 25% (w/v); and D. an appropriate amount of water.

The O/W emulsion composition for eye drops according to a second embodiment of the present invention preferably comprises the following components A to D.

A. clobetasone butyrate in an amount ranging from 0.001 to 0.05% (w/v) and preferably 0.006 to 0.05% (w/v);

B. a phospholipid in an amount ranging from 5 to 85 parts by weight and preferably 10 to 25 parts by weight per one part by weight of the component A;

C. liquid paraffin in an amount ranging from 0.5 to 80 parts by weight and preferably 5 to 80 parts by weight per one part by weight of the component B and at a concentration in the O/W emulsion of not more than 25% (w/v); and D. an appropriate amount of water.

The O/W emulsion composition for eye drops according to a third embodiment of the present invention preferably comprises the following components A to D.

A. clobetasol propionate in an amount ranging from 0.001 to 0.05% (w/v) and preferably 0.01 to 0.05% (w/v);

B. a phospholipid in an amount ranging from 5 to 85 parts by weight and preferably 5 to 10 parts by weight per one part by weight of the component A;

C. liquid paraffin in an amount ranging from 0.5 to 80 parts by weight and preferably 10 to 80 parts by weight per one part by weight of the component B and at a concentration in the O/W emulsion of not more than 25% (w/v); and D. an appropriate amount of water.

The O/W emulsion composition for eye drops according to the present invention may further comprise an isotonizing agent and/or a preservative. Moreover, the composition may likewise comprise, as a stabilizer, at least one member selected from the group consisting of tocopherol and derivatives thereof, amino acids, citric acid, EDTA and pharmaceutically acceptable salts thereof.

The drug used in the O/W emulsion composition for eye drops (hereinafter referred to as simply "emulsion") according to the present invention is one member selected from the group consisting of fluorometholone (hereinafter referred to as "FLM"), clobetasone butyrate (hereinafter referred to as "CB") and clobetasol propionate (hereinafter referred to as "CP") and the concentration thereof in the emulsion in general ranges from 0.001 to 0.05% (w/v). Even if the concentration of the drug in the emulsion is increased to a level of greater than 0.05% (w/v), the concentration of these drugs to be solubilized in the tear fluid is not improved any more. On the other hand, if the drug concentration therein is less than 0.001 (w/v), the concentration of the drug solubilized in the tear fluid is low. In this connection, the preferred range of the drug concentration in the composition varies depending on the kind of the drug to be incorporated into the composition.

When FLM is incorporated into the composition as such a drug, the concentration thereof in the composition preferably ranges from 0.005 to 0.05% (w/v). If FLM is used in an amount falling within the range defined above, an emulsion can be prepared, which can ensure a particularly high concentration of FLM dissolved in the tear fluid.

When CB is incorporated into the composition as such a drug, the concentration thereof in the composition preferably ranges from 0.006 to 0.05% (w/v). If CB is used in an amount falling within the range defined above, an emulsion can be obtained, which can ensure a particularly high concentration of CB dissolved in the tear fluid.

When CP is incorporated into the composition as such a drug, the concentration thereof in the composition preferably ranges from 0.01 to 0.05% (w/v). If CP is used in an amount falling within the range defined above, an emulsion can be obtained, which can ensure a particularly high concentration of CP dissolved in the tear fluid.

The "phospholipids" usable in the present invention are not restricted to specific ones and examples thereof include yolk lecithin, soybean lecithin and lyso-forms and hydrogenated products of these lecithins, phosphatidylcholine, phosphatidylethanolamine, phosphatidylserine, phosphatidylinositol, phosphatidylglycerol, dicetyl phosphate, sphingomyelin, synthetic phospholipids such as dimyristoyl phosphatidylcholine, dipalmitoyl phosphatidylcholine or distearoyl phosphatidylcholine, and mixtures of these phospholipids.

These phospholipids have been put on the market under the trade names of, for instance, Coatsome (registered trademark) NC-10S (high purity yolk lecithin, available from Nippon Oil and Fats Co., Ltd.), Purified Yolk Lecithin (available from Asahi Chemical Industry Co., Ltd.), Yolk Lecithin PL-100H, PL-100E, PL-100LE and PC-98N (available from Q.P. Corporation), Powdery Yolk Lecithin (hydrogenated and purified yolk lecithin) R-27, R-20 and R-5 (available from Asahi Chemical Industry Co., Ltd.), Coatsome (registered trademark) NC-21 (high purity hydrogenated soybean lecithin, available from Nippon Oil and Fats Co., Ltd.), and Yolk Lecithin LPL-20 and Sphingolipid CB-1 (available from Q. P. Corporation) and can easily be commercially available.

The preferred amount of the phospholipid used in the emulsion of the present invention may vary depending on the kind of the drug to be incorporated into the emulsion.

In general, the amount of the phospholipids to be used in the emulsion when FLM is incorporated thereinto preferably ranges from 10 to 240 parts by weight, more preferably 20 to 100 parts by weight and most preferably 25 to 75 parts by weight per one part by weight of FLM. If the phospholipids are used in an amount of not more than 240 parts by weight per one part by weight of FLM, an emulsion can be prepared, which can ensure a particularly high concentration of FLM dissolved in the tear fluid. If the amount of the phospholipid to be used is less than 10 parts by weight per one part by weight of FLM, FLM crystals are easily formed within the resulting emulsion and it is difficult to prepare an emulsion having an intended FLM concentration. On the other hand, if the amount of the phospholipid to be used is more than 240 parts by weight per one part by weight of FLM, the concentration of FLM dissolved in the tear fluid is low.

The amount of the phospholipids to be used in the emulsion when CB is incorporated thereinto preferably ranges from 5 to 85 parts by weight and more preferably 10 to 25 parts by weight per one part by weight of CB. The emulsion containing the phospholipids in an amount ranging from 10 to 25 parts by weight per one part by weight of CB permits the preparation of an emulsion which ensures a particularly high concentration of CB dissolved in the tear fluid. If the amount of the phospholipid to be used is less than 5 parts by weight per one part by weight of CB, CB crystals are easily formed within the resulting emulsion and it is difficult to prepare an emulsion having an intended CB concentration. On the other hand, if the amount of the phospholipid to be used is more than 85 parts by weight per one part by weight of CB, the concentration of CB dissolved in the tear fluid is low.

The amount of the phospholipids to be used in the emulsion when CP is incorporated thereinto preferably ranges from 5 to 85 parts by weight and more preferably 5 to 10 parts by weight per one part by weight of CB. The emulsion containing the phospholipids in an amount ranging from 5 to 10 parts by weight per one part by weight of CP permits the preparation of an emulsion which ensures a particularly high concentration of CP dissolved in the tear fluid. If the amount of the phospholipid to be used is less than 5 parts by weight per one part by weight of CP, CP crystals are easily separated out of the resulting emulsion and it is difficult to prepare an emulsion having an intended CP concentration. On the other hand, if the amount of the phospholipid to be used is more than 85 parts by weight per one part by weight of CP, the concentration of CP dissolved in the tear fluid is low.

Moreover, these phospholipids may comprise emulsifying adjuvants. Examples of such emulsifying adjuvants include phosphatidic acid, sterols such as cholesterol, aliphatic amines such as stearylamine, saturated or unsaturated fatty acids such as stearic acid, palmitic acid, myristic acid, linoleic acid and oleic acid, and pharmaceutically acceptable salts thereof (such as sodium and potassium salts). The amount of these emulsifying adjuvants to be used is in general not more than 0.2 part by weight per one part by weight of the phospholipid.

The "liquid paraffin" used in the present invention is not restricted to specific ones and specific examples thereof include light liquid paraffin (specific gravity (20/20° C. ranging from 0.830 to 0.870; kinematic viscosity (as determined at 37.8° C.) of less than 37 cst) and liquid paraffin (specific gravity (20/20° C.) ranging from 0.860 to 0.890; kinematic viscosity (at 37.8° C.) of not less than 37 cst) as described in Japanese Pharmacopoeia. Such liquid paraffin products have been put on the market by, for instance, Sanko Chemical Industry Co., Ltd. under the trade names of, for instance, Light Liquid Paraffin No. 70-S, and Liquid Paraffin No. 150-S, No. 260-S and No. 350-S and may easily and commercially be available.

In the present invention, the amount of liquid paraffin varies depending on the kind of the drug to be incorporated into the emulsion.

The amount of liquid paraffin when incorporating FLM as the drug into the emulsion preferably ranges from 0.5 to 20 parts by weight, more preferably 3 to 20 parts by weight and most preferably 4 to 15 parts by weight per one part by weight of the phospholipid, and the concentration of liquid paraffin in the emulsion is preferably not more than 25% (w/v). If the liquid paraffin is used in an amount of not less than 0.5 part by weight per one part by weight of the phospholipid and when incorporating FLM into the emulsion, an emulsion can be prepared, which may ensure a particularly high concentration of FLM dissolved in the tear fluid. If the amount of the liquid paraffin to be used upon incorporation of FLM is less than 0.5 part by weight per one part by weight of the phospholipid, the phospholipid present in the emulsion is susceptible to oxidation and the resulting emulsion is insufficient in stability. On the other hand, if the amount of the liquid paraffin to be used upon incorporation of FLM is more than 20 parts by weight per one part by weight of the phospholipid, the emulsion system is liable to be easily destroyed and thus the system is quite unstable. Moreover, if the liquid paraffin concentration in the emulsion is not less than 25%, the resulting emulsion is in a cream-like state and this impairs the feeling when the emulsion is dropped in the eyes.

The amount of liquid paraffin when incorporating CB as the drug into the emulsion preferably ranges from 0.5 to 80 parts by weight and more preferably 5 to 80 parts by weight per one part by weight of the phospholipid, and the concentration of liquid paraffin in the emulsion is preferably not more than 25% (w/v). If the liquid paraffin is used in an amount of not less than 5 parts by weight per one part by weight of the phospholipid and when incorporating CB into the emulsion, an emulsion can be prepared, which may ensure a particularly high concentration of CB dissolved in the tear fluid. If the amount of the liquid paraffin to be used upon incorporation of CB is less than 0.5 part by weight per one part by weight of the phospholipid, the phospholipid present in the emulsion is susceptible to oxidation and the resulting emulsion is insufficient in stability, while if the amount of the liquid paraffin to be used upon incorporation of CB is more than 80 parts by weight per one part by weight of the phospholipid, the emulsion system is liable to be easily destroyed and accordingly, the system is quite unstable. Moreover, if the liquid paraffin concentration in the emulsion is not less than 25%, the resulting emulsion is in a cream-like state and this impairs the feeling when the emulsion is dropped in the eyes.

The amount of liquid paraffin when incorporating CP as the drug into the emulsion preferably ranges from 0.5 to 80 parts by weight and more preferably 10 to 80 parts by weight per one part by weight of the phospholipid, and the concentration of liquid paraffin in the emulsion is preferably not more than 25% (w/v). If the liquid paraffin is used in an amount of not less than 10 parts by weight per one part by weight of the phospholipid and when incorporating CP into the emulsion, an emulsion can be prepared, which may ensure a particularly high concentration of CP dissolved in the tear fluid. If the amount of the liquid paraffin to be used upon incorporation of CP is less than 0.5 part by weight per one part by weight of the phospholipid, the phospholipid present in the emulsion is susceptible to oxidation and the resulting emulsion is insufficient in stability, while if the amount of the liquid paraffin to be used upon incorporation of CP is more than 80 parts by weight per one part by weight of the phospholipid, the emulsion system is liable to be easily destroyed and accordingly, the system is quite unstable. Moreover, if the liquid paraffin concentration in the emulsion is not less than 25%, the resulting emulsion is in a cream-like state and this impairs the feeling when the emulsion is dropped in the eyes.

When preparing the emulsion of the present invention, there may be added, to the essential component of the present invention, i.e., water, liquid paraffin or a phospholipid, sugars such as xylitol, mannitol and glucose; isotonizing agent such as propylene glycol and glycerol; pH adjusting agents such as sodium hydroxide and hydrochloric acid; preservatives such as chlorobutanol, and parabens such as methyl p-hydroxybenzoate and propyl p-hydroxybenzoate; and/or thickeners such as methyl cellulose, hydroxypropylmethyl cellulose, hydroxyethyl cellulose, polyvinyl pyrrolidone, polyvinyl alcohol, propylene glycol, diethylene glycol and sodium polyacrylate, insofar as they do not impair the effect of the present invention.

To the essential component of the present invention, i.e., water, liquid paraffin or a phospholipid, there may also be added at least one member selected from the group consisting of stabilizers such as amino acids, citric acid, EDTA (ethylenediaminetetraacetic acid) and pharmaceutically acceptable salts thereof, tocopherol and derivatives thereof and gelatin in an amount which does not impair the effect of the present invention.

Examples of amino acids usable in the present invention are histidine and pharmaceutically acceptable salts thereof (such as hydrochloride), methionine, phenylalanine and serine.

Examples of pharmaceutically acceptable salts of citric acid usable in the present invention are sodium and potassium salts of citric acid.

Examples of pharmaceutically acceptable salts of EDTA usable in the present invention are sodium edetate, tetrasodium edetate, tetrasodium edetate tetrahydrate and disodium calcium edetate.

Examples of tocopherol derivatives usable in the present invention are tocopherol acetate, tocopherol nicotinate and tocopherol succinate.

The emulsion of the present invention may be subjected to a sterilization treatment such as sterilization by filtration through a membrane or fractional sterilization.

In order to store the emulsion of the present invention over a long time period, the emulsion may be filled in an eye drop bottle and then pillow-packaged in a laminate bag of a polyethylene film with an aluminum foil together with a deoxygenating agent (such as Ageless (registered trademark), available from Mitsubishi Gas Chemical Co., Inc.).

The emulsion of the present invention is in general prepared so as to have a pH ranging from 4.5 to 8.5, and preferably from 6.0 to 8.0 from the viewpoint of the ocular irritation thereof.

Then the method for preparing the emulsion of the present invention will be explained below. A variety of known methods may be employed and, for instance, the emulsion of the present invention may be prepared by dissolving, with stirring, phospholipids such as yolk lecithin and, if desired, phosphatidylethanolamine and emulsifying adjuvants such as oleic acid, and a drug selected from FLM, CB and CP in an appropriate organic solvent such as hexane or ethanol, followed by distilling off the solvent under reduced pressure to thus form a thin film of the lipid. To the resulting thin film, there are added liquid paraffin and water and then the mixture is vigorously shaken and stirred to carry out pre-emulsification. The resulting liquid is emulsified in an emulsifier commonly used. To the liquid obtained after the emulsification, there may be added, for instance, a preservative and a stabilizer, followed by adjusting the pH value thereof to a desired level using HCl or NaOH to thus give an FLM, CB or CP-containing O/W emulsion according to the present invention. Further, the resulting emulsion is filled in an eye drop bottle, followed by sterilization to give an eye drop according to the present invention.

The present invention will hereinafter be described in more detail with reference to the following Examples and Test Examples.

EXAMPLES

The drug instilled in the eyes is rapidly cleared from the surface of the eyes which are principal absorption sites of the drug due to, for instance, the turnover of the tear fluid and accordingly, the evaluation of solubility of FLM, CB and CP in the tear fluid requires the use of a method capable of determining the amounts of FLM, CB and CP dissolved in the tear fluid within a short period of time. Thus, the evaluation of solubility of FLM, CB and CP in the tear fluid was performed according to the following method.

As a substitute (artificial tear fluid) for the tear fluid, there was used PBS (composition: NaCl 0.8% (w/v); KCl 0.02% (w/v); $Na_2HPO_4$ 0.115% (w/v); $KH_2PO_4$ 0.02% (w/v); pH 7.4) currently used in biochemical tests. This PBS was introduced into a 15 ml test tube equipped with a cap and held in a thermostatic chamber maintained at 36° C. Then a predetermined amount of the emulsion was added to the foregoing PBS and the test tube was gently shaken and turned round for 30 seconds. In this respect, the amounts of the emulsion and PBS were as follows:

| Dilution Factor | FLM-Containing Emulsion of the Present Invention (ml) | PBS (ml) |
| --- | --- | --- |
| 5 | 1.0 | 4.0 |
| 10 | 0.5 | 4.5 |
| 21 | 0.2 | 4.0 |
| 51 | 0.1 | 5.0 |

| Dilution Factor | CB- or CP-Containing Emulsion of the Present Invention (ml) | PBS (ml) |
| --- | --- | --- |
| 21 | 0.25 | 5.0 |
| 41 | 0.25 | 10.0 |
| 101 | 0.1 | 10.0 |

The PBS to which the emulsion had been added (0.4 ml) was immediately dispensed (within 3 minutes after the addition of the emulsion to PBS) in a ultrafiltration kit (Ultrafree C3LTK available from Millipore Company), followed by separation of PBS (8500 rpm, 5 minutes) in which FLM, CB or CP was dissolved from the emulsion using a centrifugal separator (MS-150 available from Tomy Seiko Co., Ltd.). FLM, CB and CP present in the separated PBS were quantitatively analyzed using the HPLC technique to thus determine the concentrations of FLM, CB and CP (Dissolved FLM Concn.; Dissolved CB Concn. and Dissolved CP Concn.) dissolved in the PBS (artificial tear fluid).

Example 1

Yolk lecithin [Coatsome (registered trademark) NC-10S, phosphatidylcholine 95%, available from Nippon Oil and Fats Co., Ltd. (hereinafter referred to as "EPC")] and purified yolk lecithin [phosphatidylcholine 70%, phosphatidylethanolamine 20%, available from Asahi Chemical Industry Co., Ltd. (hereinafter referred to as "PYL")] were dissolved in a hexane/ethanol (10/1 (v/v)) mixed solvent, in a weight ratio of 7:3. Separately FLM was dissolved in ethanol, then the resulting solution was admixed with the foregoing phospholipid solution, followed by distilling off the solvent using an evaporator and subsequently a vacuum pump to form a thin film of the FLM-containing phospholipid. To the phospholipid thin film, there were added liquid paraffin (No. 260-S available from Sanko Chemical Industry Co., Ltd.) and a 2% aqueous glycerol solution and the resulting mixture was pre-emulsified by vigorously shaking and stirring the same. After adding additional amount of a 2% aqueous glycerol solution to the pre-emulsified solution up to a total volume of 100 ml, the mixture was emulsified using a microfluidizer (M-110EH available from Microfluidics Company) by passing 30 times therethrough while applying a pressure of 750 $kg/cm^2$. After completion of the emulsification, a 1N NaOH solution was added to control the pH value to 6.5 to 7.5 and to thus give an FLM-containing emulsion according to the present invention.

Table 1 shows the formulations of the FLM-containing emulsion of the present invention (hereinafter referred to as simply "FLM emulsion") and dissolved FLM concentrations observed when these emulsions and commercially available FLM suspensions (Flumetholon (registered trademark) 0.1 and 0.02, available from Santen Pharmaceutical Co., Ltd.) as comparative examples were diluted with PBS.

The FLM emulsions showed very high dissolved FLM concentrations irrespective of the dilution factor with PBS. These results indicate that the emulsion of the present invention which comprises FLM, phospholipid, liquid paraffin and water is excellent in solubility of FLM in the artificial tear fluid. Incidentally, the following tests of FLM-solubilization ability were carried out at a dilution factor for the FLM emulsions of 51 times.

TABLE 1

| Formulation | Phospholipid % (w/v) | Liquid Paraffin % (w/v) | FLM Concn. % (w/v) |
|---|---|---|---|
| 1 | 0.35 | 3.5 | 0.02 |
| 2 | 0.75 | 7.5 | 0.02 |
| 3 | 1.50 | 15.0 | 0.02 |
| 4 | Suspension (Flumetholon 0.02) | | 0.02 |
| 5 | Suspension (Flumetholon 0.1) | | 0.10 |

| | Dissolved FLM Concn. (μg/ml) | | | |
|---|---|---|---|---|
| | Dilution Factor | | | |
| Formulation | 5 | 10 | 21 | 51 |
| 1 | 11.84 | 6.92 | 4.24 | 2.64 |
| 2 | 14.92 | 10.86 | 5.73 | 3.19 |
| 3 | 8.78 | 6.20 | 4.82 | 2.64 |
| 4 | 2.18 | 2.02 | 1.42 | 0.73 |
| 5 | 2.73 | 2.37 | 1.94 | 1.54 |

Dissolution Test: The FLM emulsion was diluted from 5 to 51 times with PBS.
Phospholipid: EPC:PYL = 7:3 (weight ratio)

Example 2

The same procedures used in Example 1 were repeated except that the FLM concentration of Formulation 1 was variously changed within the range of from 0.001 to 0.06% (w/v) to give FLM emulsions. Table 2 shows the formulations of these emulsions and dissolved FLM concentrations observed when these emulsions and commercially available Suspensions as comparative examples were diluted 51 times with PBS.

Although the dissolved FLM concentration increased in proportion to the FLM concentration in each FLM emulsion, but if it reached 0.05% (w/v), the dissolved FLM concentration did not increase any more. This clearly indicates that the FLM concentration in the FLM emulsion is preferably not more than 0.05% (w/v).

TABLE 2

| Formulation | Phospholipid % (w/v) | Liquid Paraffin % (w/v) | FLM Concn. % (w/v) | Dissolved FLM Concn. (μg/ml) |
|---|---|---|---|---|
| 6 | 0.04 | 0.4 | 0.001 | 0.09 |
| 7 | 0.08 | 0.8 | 0.002 | 0.27 |

TABLE 2-continued

| Formulation | Phospholipid % (w/v) | Liquid Paraffin % (w/v) | FLM Concn. % (w/v) | Dissolved FLM Concn. (μg/ml) |
|---|---|---|---|---|
| 8 | 0.16 | 1.6 | 0.004 | 0.60 |
| 9 | 0.21 | 2.1 | 0.005 | 0.80 |
| 10 | 0.42 | 4.2 | 0.01 | 1.51 |
| 11 | 0.84 | 8.4 | 0.02 | 3.19 |
| 12 | 1.19 | 12.0 | 0.03 | 3.90 |
| 13 | 1.44 | 14.4 | 0.04 | 4.42 |
| 14 | 2.00 | 20.0 | 0.05 | 4.87 |
| 15 | 2.20 | 22.0 | 0.06 | 4.88 |
| 16 | 2.40 | 24.0 | 0.06 | 4.76 |
| 4 | Suspension (Flumetholon 0.02) | | 0.02 | 0.73 |
| 5 | Suspension (Flumetholon 0.1) | | 0.10 | 1.54 |

Dissolution Test: The FLM emulsion was diluted 51 times with PBS.
Phospholipid: EPC:PYL = 7:3 (weight ratio)

Example 3

The same procedures used in Example 1 were repeated except that the FLM, phospholipid and liquid paraffin concentrations were variously changed to give FLM emulsions. Table 3 shows the formulations of these emulsions and dissolved FLM concentrations observed when these emulsions were diluted 51 times with PBS.

These experiments indicate that the dissolved FLM concentration varies depending on the FLM concentration in the FLM emulsion, the weight ratio of phospholipid to FLM and the weight ratio of liquid paraffin to phospholipid. In particular, the FLM emulsion excellent in the FLM-solubilization ability is those comprising:

A. 0.005 to 0.05% (w/v) of fluorometholone;

B. 10 to 240 parts by weight of phospholipid per one part by weight of the component A; and C. 0.5 to 20 parts by weight of liquid paraffin per one part by weight of the component B.

TABLE 3

| Formulation | Phospholipid % (w/v) | Liquid Paraffin % (w/v) | FLM Concn. % (w/v) | Ratio Lip/ FLM | Ratio L.P./ Lip | Dissolved FLM Concn. (μg/ml) |
|---|---|---|---|---|---|---|
| 17 | 0.05 | 0.25 | 0.005 | 10 | 5 | 0.59 |
| 18 | 0.05 | 0.84 | 0.005 | 10 | 16.8 | 0.63 |
| 19 | 0.10 | 0.50 | 0.005 | 20 | 5 | 0.70 |
| 20 | 0.10 | 2.00 | 0.005 | 20 | 20 | 0.61 |
| 21 | 0.13 | 0.50 | 0.005 | 25 | 4 | 0.71 |
| 22 | 0.13 | 1.88 | 0.005 | 25 | 15 | 0.72 |
| 23 | 0.15 | 0.38 | 0.005 | 30 | 2.5 | 0.60 |
| 24 | 0.15 | 3.00 | 0.005 | 30 | 20 | 0.67 |
| 25 | 0.20 | 0.20 | 0.005 | 40 | 1 | 0.62 |
| 26 | 0.20 | 0.60 | 0.005 | 40 | 3 | 0.73 |
| 27 | 0.20 | 0.80 | 0.005 | 40 | 4 | 0.73 |
| 28 | 0.20 | 3.00 | 0.005 | 40 | 15 | 0.72 |
| 29 | 0.25 | 2.50 | 0.005 | 50 | 10 | 0.79 |
| 30 | 0.38 | 0.19 | 0.005 | 75 | 0.5 | 0.63 |
| 31 | 0.38 | 0.94 | 0.005 | 75 | 2.5 | 0.74 |
| 32 | 0.38 | 1.50 | 0.005 | 75 | 4 | 0.71 |
| 33 | 0.38 | 7.50 | 0.005 | 75 | 20 | 0.72 |
| 34 | 0.50 | 1.50 | 0.005 | 100 | 3 | 0.72 |
| 35 | 0.50 | 2.50 | 0.005 | 100 | 5 | 0.73 |
| 36 | 0.50 | 10.00 | 0.000 | 100 | 20 | 0.61 |
| 37 | 0.75 | 11.25 | 0.005 | 150 | 15 | 0.60 |
| 38 | 1.00 | 0.50 | 0.005 | 200 | 0.5 | 0.63 |
| 39 | 1.00 | 10.00 | 0.005 | 200 | 10 | 0.62 |
| 40 | 1.10 | 1.10 | 0.005 | 220 | 1 | 0.63 |
| 41 | 1.10 | 5.60 | 0.005 | 220 | 5 | 0.61 |
| 42 | 1.20 | 3.00 | 0.005 | 240 | 2.5 | 0.60 |
| 43 | 0.38 | 0.09 | 0.005 | 76 | 0.24 | 0.52 |

TABLE 3-continued

| Formulation | Phospholipid % (w/v) | Liquid Paraffin % (w/v) | FLM Concn. % (w/v) | Ratio Lip/FLM | Ratio L.P./Lip | Dissolved FLM Concn. (µg/ml) |
|---|---|---|---|---|---|---|
| 44 | 1.00 | 0.25 | 0.005 | 200 | 0.25 | 0.50 |
| 45 | 1.25 | 3.13 | 0.005 | 250 | 2.5 | 0.54 |
| 46 | 1.25 | 5.00 | 0.005 | 250 | 4 | 0.46 |
| 47 | 0.20 | 2.00 | 0.02 | 10 | 10 | 1.80 |
| 48 | 0.50 | 5.00 | 0.02 | 25 | 10 | 3.02 |
| 49 | 1.00 | 10.00 | 0.02 | 50 | 10 | 3.15 |
| 50 | 2.00 | 10.00 | 0.02 | 100 | 5 | 1.79 |
| 51 | 2.00 | 20.00 | 0.02 | 100 | 10 | 2.24 |
| 52 | 0.84 | 2.10 | 0.02 | 42 | 2.5 | 1.71 |
| 53 | 0.84 | 2.50 | 0.02 | 42 | 3 | 2.26 |
| 54 | 0.84 | 4.20 | 0.02 | 42 | 5 | 3.02 |
| 55 | 0.84 | 12.60 | 0.02 | 42 | 15 | 2.90 |
| 56 | 0.84 | 16.80 | 0.02 | 42 | 20 | 2.76 |
| 57 | 0.50 | 1.50 | 0.05 | 10 | 3 | 1.97 |
| 58 | 0.50 | 10.00 | 0.05 | 10 | 20 | 3.63 |
| 59 | 1.00 | 3.00 | 0.05 | 20 | 3 | 2.08 |
| 60 | 1.00 | 10.00 | 0.05 | 20 | 10 | 4.17 |
| 61 | 1.00 | 20.00 | 0.05 | 20 | 20 | 3.67 |
| 62 | 1.25 | 12.50 | 0.05 | 25 | 10 | 4.64 |
| 63 | 1.25 | 18.75 | 0.05 | 25 | 15 | 4.61 |
| 64 | 1.25 | 25.00 | 0.05 | 25 | 20 | 3.61 |
| 65 | 1.50 | 7.50 | 0.05 | 30 | 5 | 3.93 |
| 66 | 1.50 | 15.00 | 0.05 | 30 | 10 | 4.63 |
| 67 | 2.00 | 5.00 | 0.05 | 40 | 2.5 | 2.57 |
| 68 | 2.00 | 10.00 | 0.05 | 40 | 5 | 4.27 |
| 69 | 2.00 | 15.00 | 0.05 | 40 | 7.5 | 4.58 |
| 70 | 2.00 | 25.00 | 0.05 | 40 | 12.5 | 3.81 |
| 71 | 2.50 | 2.50 | 0.05 | 50 | 1 | 1.97 |
| 72 | 2.50 | 7.50 | 0.05 | 50 | 3 | 4.29 |
| 73 | 2.50 | 10.00 | 0.05 | 50 | 4 | 4.44 |
| 74 | 2.50 | 25.00 | 0.05 | 50 | 10 | 3.94 |
| 75 | 3.75 | 1.88 | 0.05 | 75 | 0.5 | 2.63 |
| 76 | 3.75 | 9.38 | 0.05 | 75 | 2.5 | 3.96 |
| 77 | 3.75 | 15.00 | 0.05 | 75 | 4 | 4.09 |
| 78 | 5.00 | 15.00 | 0.05 | 100 | 3 | 4.04 |
| 79 | 5.00 | 25.00 | 0.05 | 100 | 5 | 3.27 |
| 80 | 7.50 | 18.75 | 0.05 | 150 | 2.5 | 2.84 |
| 81 | 10.00 | 25.00 | 0.05 | 200 | 2.5 | 1.99 |
| 82 | 3.75 | 0.94 | 0.05 | 75 | 0.25 | 1.77 |
| 83 | 4.25 | 1.06 | 0.05 | 85 | 0.25 | 1.41 |

Dissolution Test: The FLM emulsion was diluted 51 times with PBS.
Phospholipid: EPC:PYL = 7:3 (weight ratio)
Lip/FLM: phospholipid (% (w/v))/FLM(% (w/v))
L.P./Lip: liquid paraffin (% (w/v))/phospholipid (% (w/v))

Example 4

The same procedures used in Example 1 were repeated except that the liquid paraffin formulation shown in Table 4 was substituted for the liquid paraffin used in the formulation 50 to give FLM emulsions. Table 4 shows the formulations of these emulsions and dissolved FLM concentrations observed when these emulsions were diluted 51 times with PBS.

The FLM emulsions which comprised liquid paraffin products having different specific gravities and kinematic viscosities are all excellent in the FLM-solubilization ability.

TABLE 4

| Formulation | Phospholipid % (w/v) | Grade of Liquid Paraffin % (w/v) | FLM Concn. % (w/v) | Dissolved FLM Concn. (µg/ml) |
|---|---|---|---|---|
| 84 | 2.00 | No. 70-S 10.00 | 0.02 | 1.54 |
| 85 | 2.00 | No. 150-S 10.00 | 0.02 | 1.85 |
| 50 | 2.00 | No. 260-S 10.00 | 0.02 | 1.79 |
| 86 | 2.00 | No. 350-S 10.00 | 0.02 | 1.87 |

Dissolution Test: The FLM emulsion was diluted 51 times with PBS.
Phospholipid: EPC:PYL = 7:3 (weight ratio)
Liquid Paraffin:
light liquid paraffin No. 70-S [kinematic viscosity 14.10 cst (at 37.8° C.); specific gravity (20/20° C.) 0.841, available from Sanko Chemical Industry Co., Ltd.]
liquid paraffin No. 150-S [kinematic viscosity 28.00 cst (at 37.8° C.); specific gravity (20/20° C.) 0.854, available from Sanko Chemical Industry Co., Ltd.]
liquid paraffin No. 260-S [kinematic viscosity 56.50 cst (at 37.8° C.); specific gravity (20/20° C.) 0.861, available from Sanko Chemical Industry Co., Ltd.]
liquid paraffin No. 350-S [kinematic viscosity 77.00 cst (at 37.8° C.); specific gravity (20/20° C.) 0.876, available from Sanko Chemical Industry Co., Ltd.]

Example 5

The same procedures used in Example 1 were repeated except that mixtures of phospholipids and emulsifying adjuvant having the formulation shown in Table 5 were substituted for the phospholipid used in the formulation 11 to thus give FLM emulsions. Table 5 shows the formulations of these emulsions and dissolved FLM concentrations observed when these emulsions were diluted 51 times with PBS.

These FLM emulsions to which a variety of emulsifying adjuvants were added are all excellent in the FLM-solubilization ability.

TABLE 5

| Formulation | Formulation of Phospholipid and Emulsifying Adjuvants % (w/v) | Liquid Paraffin % (w/v) | FLM Concn. % (w/v) | Dissolved FLM Concn. (µg/ml) |
|---|---|---|---|---|
| 87 | EPC(0.84) | 8.4 | 0.02 | 2.25 |
| 88 | PYL(0.84) | 8.4 | 0.02 | 3.21 |
| 89 | EPC(0.59), PYL(0.25), PCS(0.08) | 8.4 | 0.02 | 3.19 |
| 90 | EPC(0.59), PYL(0.25), PCEH(0.08) | 8.4 | 0.02 | 2.67 |
| 91 | EPC(0.59), PYL(0.25), MC(0.08) | 8.4 | 0.02 | 3.12 |
| 92 | EPC(0.59), PYL(0.25), MA(0.08) | 8.4 | 0.02 | 3.00 |
| 93 | EPC(0.59), PYL(0.25), MGL(0.08) | 8.4 | 0.02 | 3.07 |
| 94 | EPC(0.59), PYL(0.25), OA(0.04) | 8.4 | 0.02 | 2.98 |
| 95 | EPC(0.59), PYL(0.25), chol(0.08) | 8.4 | 0.02 | 3.18 |
| 96 | EPC(0.59), PYL(0.25), PLA(0.08) | 8.4 | 0.02 | 2.17 |

Dissolution Test: The FLM emulsion was diluted 51 times with PBS.

TABLE 5-continued

| Formulation | Formulation of Phospholipid and Emulsifying Adjuvants % (w/v) | Liquid Paraffin % (w/v) | FLM Concn. % (w/v) | Dissolved FLM Concn. (μg/ml) |
|---|---|---|---|---|

Formulation of Phospholipid-Emulsifying Adjuvants
PCS: Soybean lecithin (phosphatidylcholine 97%, available from Nippon Pure Chemical Co., Ltd.)
PCEH: Hydrogenated yolk phosphatidylcholine (available from Nippon Pure Chemical Co., Ltd.)
MC: Dipalmitoyl phosphatidylcholine (MC 6060, available from Nippon Oil and Fats Co., Ltd.)
MA: Dipalmitoyl phosphatidic acid (MA 6060, available from Nippon Oil and Fats Co., Ltd.)
MGL: Dipalmitoyl phosphatidyl glycerol (MGLS 6060, available from Nippon Oil and Fats Co., Ltd.)
OA: Oleic acid
chol: Cholesterol
PLA: Palmitic acid

Example 6

The same procedures used in Example 1 were repeated except that α-tocopherol acetate was added to the phospholipid of the formulation 11 to thus give FLM emulsions. Separately, the same procedures used in Example 1 were repeated except that α-tocopherol acetate was added to the liquid paraffin of the formulation 11 to thus give FLM emulsions.

Table 6 shows the formulations of these emulsions and dissolved FLM concentrations observed when these emulsions were diluted 51 times with PBS.

These FLM emulsions to which α-tocopherol acetate was added are all excellent in the FLM-solubilization ability.

TABLE 6

| Formulation | Phospholipid Formulation % (w/v) | Oil Formulation % (w/v) | FLM Concn. % (w/v) | Dissolved FLM Concn. (μg/ml) |
|---|---|---|---|---|
| 97 | EPC(0.59), PYL(0.25), toc(0.04) | L.P.(8.40) | 0.02 | 3.15 |
| 98 | EPC(0.59), PYL(0.25) | L.P.(8.40), toc(0.084) | 0.02 | 2.63 |

Dissolution Test: The FLM emulsion was diluted 51 times with PBS.
L.P.: liquid paraffin
toc: α-tocopherol acetate

Example 7

To a 2% aqueous glycerol solution (pH 6.0) containing 0.5% (w/v) chlorobutanol, 0.1% (w/v) histidine and 0.04% (w/v) citric acid, there was added an equal volume of the FLM emulsion according to the formulation 11 followed by sufficient mixing of the resulting mixture. After adjusting the pH of this mixed solution to 6.0 with HCl, it was filtered through a membrane having a pore size of 0.45 μm to thus prepare an FLM emulsion containing the foregoing additives. The resulting emulsion was filled in an eye drop bottle, then thermally sterilized according to the fractional sterilization method to thus give an eye drop of the present invention. The resulting eye drop of the present invention and Ageless (registered trademark) Z (available from Mitsubishi Gas Chemical Co., Inc.) were packaged together in a laminate bag of a polyethylene film and an aluminum foil according to the pillow-packaging technique.

Example 8

To a 2% aqueous glycerol solution (pH 7.0) containing 0.052% (w/v) methyl p-hydroxybenzoate, 0.028% (w/v) propyl p-hydroxybenzoate and 0.01% (w/v) EDTA .2Na, there was added an equal volume of the FLM emulsion according to the formulation 11 followed by sufficient mixing of the resulting mixture. After adjusting the pH of this mixture to 7.0 with NaOH, it was filtered through a membrane having a pore size of 0.45 μm to thus prepare an FLM emulsion containing the foregoing additives. The resulting emulsion was filled in an eye drop bottle, then thermally sterilized according to the fractional sterilization method to thus give an eye drop of the present invention.

Example 9

The same procedures for preparing emulsions disclosed in Example 1 were repeated except that CB was substituted for FLM to thus prepare CB-containing emulsions according to the present invention. The following Table 7 shows the formulations of the CB-containing emulsions of the present invention (hereinafter referred to as simply "CB emulsion") and the dissolved CB concentrations observed when these CB emulsions and commercially available CB Suspensions [CLOBURATE (registered trademark), 0.1% (w/v) CB, available from Cusi (UK) Ltd.] were diluted with PBS.

The CB emulsions showed very high dissolved CB concentrations irrespective of the dilution factor with PBS. These results indicate that the emulsion of the present invention which comprises CB, phospholipid, liquid paraffin and water is excellent in solubility of CB in the artificial tear fluid. Incidentally, the following tests of the CB-solubilization ability were carried out at a dilution factor for the CB emulsions of 41 times.

TABLE 7

| Formulation | Phospholipid % (w/v) | Liquid Paraffin % (w/v) | CB Concn. % (w/v) |
|---|---|---|---|
| 99 | 0.30 | 24.0 | 0.01 |
| 100 | 0.20 | 9.00 | 0.02 |
| 101 | 0.40 | 18.00 | 0.02 |
| 102 | 0.90 | 25.00 | 0.03 |
| 103 | Suspension | | 0.1 |

| | Dissolved CB Concn. (μg/ml) | | |
|---|---|---|---|
| | Dilution Factor | | |
| Formulation | 21 | 41 | 101 |
| 99 | 0.41 | 0.35 | 0.30 |
| 100 | 1.08 | 0.87 | 0.68 |
| 101 | 0.61 | 0.46 | 0.32 |
| 102 | 0.33 | 0.22 | 0.12 |
| 103 | 0.24 | 0.17 | 0.09 |

Dissolution Test: The CD emulsion was diluted from 21 to 101 times with PBS.
Phospholipid: EPC:PYL = 7:3 (weight ratio)
Suspension: CLOBURATE (registered trademark) (CB-suspended eye drop, 0.1% (w/v) CB, available from Cusi (UK) Ltd.)

Example 10

The same procedures used in Example 9 were repeated except that the CB concentration was variously changed within the range of from 0.0008 to 0.1% (w/v) to give CB emulsions. Table 8 shows the formulations of these CB emulsions and dissolved CB concentrations observed when these emulsions and commercially available Suspensions as comparative examples were diluted 41 times with PBS.

Although the dissolved CB concentration increased in proportion to the CB concentration in each CB emulsion, but if it reached 0.05% (w/v), the dissolved CB concentration did not increase any more. This clearly indicates that the CB concentration in the CB emulsion is preferably not more than 0.05% (w/v).

TABLE 8

| Formulation | Phospholipid % (w/v) | Liquid Paraffin % (w/v) | CB Concn. % (w/v) | Dissolved CB Concn. (μg/ml) |
|---|---|---|---|---|
| 104 | 0.008 | 0.36 | 0.0008 | 0.10 |
| 105 | 0.012 | 0.54 | 0.0012 | 0.17 |
| 106 | 0.025 | 1.13 | 0.0025 | 0.15 |
| 107 | 0.05 | 2.25 | 0.005 | 0.30 |
| 108 | 0.06 | 2.70 | 0.006 | 0.56 |
| 109 | 0.10 | 4.50 | 0.01 | 0.68 |
| 100 | 0.20 | 9.00 | 0.02 | 0.87 |
| 110 | 0.50 | 22.50 | 0.05 | 0.98 |
| 111 | 0.40 | 4.00 | 0.02 | 0.35 |
| 112 | 1.00 | 10.00 | 0.05 | 0.36 |
| 113 | 1.60 | 16.00 | 0.08 | 0.25 |
| 114 | 2.00 | 20.00 | 0.1 | 0.21 |
| 115 | 0.60 | 6.00 | 0.02 | 0.27 |
| 116 | 1.50 | 15.00 | 0.05 | 0.28 |
| 117 | 3.00 | 30.00 | 0.1 | 0.23 |
| 103 | Suspension | | 0.1 | 0.17 |

Dissolution Test: The CB emulsion was diluted 41 times with PBS.
Phospholipid: EPC:PYL = 7:3 (weight ratio)
Suspension: CLOBURATE (registered trademark) (CB-suspended eye drop, 0.1% (w/v) CB, available from Cusi (UK) Ltd.)

Example 11

The same procedures used in Example 9 were repeated except that the CB, phospholipid and liquid paraffin concentrations were variously changed to give CB emulsions. Table 9 shows the formulations of these emulsions and dissolved CB concentrations observed when these emulsions were diluted 41 times with PBS.

These experiments indicate that the dissolved CB concentration varies depending on the CB concentration in the CB emulsion, the weight ratio of phospholipid to CB and the weight ratio of liquid paraffin to phospholipid. In particular, the CB emulsion excellent in the CB-solubilization ability is those comprising:

A. 0.006 to 0.05% (w/v) of clobetasone butyrate;
B. 10 to 25 parts by weight of phospholipid per one part by weight of the component A; and
C. 5 to 80 parts by weight of liquid paraffin per one part by weight of the component B.

TABLE 9

| Formulation | Phospholipid %(w/v) | Liquid Paraffin %(w/v) | CB Concn. %(w/v) | Ratio Lip/CB | Ratio L.P./Lip | Dissolved CB Concn. (μg/ml) |
|---|---|---|---|---|---|---|
| 118 | 0.025 | 0.25 | 0.0025 | 10 | 10 | 0.15 |
| 106 | 0.025 | 1.13 | 0.0025 | 10 | 45 | 0.15 |
| 119 | 0.05 | 4.00 | 0.0025 | 20 | 80 | 0.12 |
| 120 | 0.063 | 0.63 | 0.0025 | 25 | 10 | 0.13 |
| 121 | 0.03 | 0.30 | 0.003 | 10 | 10 | 0.15 |
| 122 | 0.03 | 1.95 | 0.003 | 10 | 65 | 0.39 |
| 123 | 0.06 | 0.60 | 0.003 | 20 | 10 | 0.19 |
| 124 | 0.06 | 2.70 | 0.003 | 20 | 45 | 0.25 |
| 125 | 0.06 | 4.80 | 0.003 | 20 | 80 | 0.23 |
| 107 | 0.05 | 2.25 | 0.005 | 10 | 45 | 0.30 |
| 126 | 0.05 | 4.00 | 0.005 | 10 | 80 | 0.29 |
| 127 | 0.10 | 1.00 | 0.005 | 20 | 10 | 0.21 |
| 128 | 0.15 | 1.50 | 0.005 | 30 | 10 | 0.23 |
| 129 | 0.15 | 6.75 | 0.005 | 30 | 45 | 0.23 |
| 130 | 0.20 | 9.00 | 0.005 | 40 | 45 | 0.14 |
| 131 | 0.03 | 2.40 | 0.006 | 5 | 80 | 0.51 |
| 108 | 0.06 | 2.70 | 0.006 | 10 | 45 | 0.56 |
| 132 | 0.06 | 4.80 | 0.006 | 10 | 80 | 0.34 |
| 133 | 0.09 | 0.45 | 0.006 | 15 | 5 | 0.34 |
| 134 | 0.15 | 12.00 | 0.006 | 25 | 80 | 0.23 |
| 135 | 0.05 | 4.00 | 0.01 | 5 | 80 | 0.58 |
| 109 | 0.10 | 4.50 | 0.01 | 10 | 45 | 0.68 |
| 136 | 0.10 | 8.00 | 0.01 | 10 | 80 | 0.72 |
| 137 | 0.20 | 2.00 | 0.01 | 20 | 10 | 0.25 |
| 138 | 0.20 | 5.00 | 0.01 | 20 | 25 | 0.35 |
| 139 | 0.20 | 16.00 | 0.01 | 20 | 80 | 0.39 |
| 140 | 0.30 | 0.75 | 0.01 | 30 | 2.5 | 0.ii |
| 141 | 0.30 | 1.50 | 0.01 | 30 | 5 | 0.20 |
| 99 | 0.30 | 24.00 | 0.01 | 30 | 80 | 0.35 |
| 142 | 0.35 | 24.50 | 0.01 | 35 | 70 | 0.34 |
| 143 | 0.40 | 0.20 | 0.01 | 40 | 0.5 | 0.25 |
| 144 | 0.40 | 2.00 | 0.01 | 40 | 5 | 0.28 |
| 145 | 0.40 | 24.00 | 0.01 | 40 | 60 | 0.30 |
| 146 | 0.45 | 24.75 | 0.01 | 45 | 55 | 0.22 |
| 147 | 0.10 | 5.5 | 0.02 | 5 | 55 | 0.99 |
| 100 | 0.20 | 9.00 | 0.02 | 10 | 45 | 0.87 |
| 148 | 0.30 | 3.00 | 0.02 | 15 | 10 | 0.51 |
| 149 | 0.30 | 24.00 | 0.02 | 15 | 80 | 0.48 |
| 111 | 0.40 | 4.00 | 0.02 | 20 | 10 | 0.35 |
| 150 | 0.40 | 6.00 | 0.02 | 20 | 15 | 0.48 |
| 101 | 0.40 | 18.00 | 0.02 | 20 | 45 | 0.46 |
| 151 | 0.40 | 20.00 | 0.02 | 20 | 50 | 0.56 |
| 152 | 0.40 | 24.00 | 0.02 | 20 | 60 | 0.72 |
| 153 | 0.50 | 25.00 | 0.02 | 25 | 50 | 0.63 |
| 115 | 0.60 | 6.00 | 0.02 | 30 | 10 | 0.27 |
| 154 | 0.60 | 24.00 | 0.02 | 30 | 40 | 0.33 |
| 155 | 0.70 | 3.50 | 0.02 | 35 | 5 | 0.24 |
| 156 | 0.70 | 24.50 | 0.02 | 35 | 35 | 0.26 |
| 157 | 1.00 | 2.50 | 0.02 | 50 | 2.5 | 0.34 |
| 158 | 1.30 | 25.00 | 0.02 | 65 | 19 | 0.20 |
| 159 | 1.70 | 0.85 | 0.02 | 85 | 0.5 | 0.36 |
| 160 | 1.70 | 4.25 | 0.02 | 85 | 2.5 | 0.20 |
| 161 | 0.15 | 9.75 | 0.03 | 5 | 65 | 0.97 |
| 162 | 0.30 | 19.50 | 0.03 | 10 | 65 | 1.01 |
| 163 | 0.30 | 24.00 | 0.03 | 10 | 80 | 1.00 |

TABLE 9-continued

| Formulation | Phospholipid %(w/v) | Liquid Paraffin %(w/v) | CB Concn. %(w/v) | Ratio Lip/CB | Ratio L.P./Lip | Dissolved CB Concn. (μg/ml) |
|---|---|---|---|---|---|---|
| 164 | 0.45 | 24.75 | 0.03 | 15 | 55 | 0.85 |
| 165 | 0.60 | 15.00 | 0.03 | 20 | 25 | 0.56 |
| 166 | 0.60 | 24.60 | 0.03 | 20 | 41 | 0.70 |
| 167 | 0.75 | 22.50 | 0.03 | 25 | 30 | 0.33 |
| 102 | 0.90 | 25.00 | 0.03 | 30 | 28 | 0.22 |
| 168 | 1.05 | 0.53 | 0.03 | 35 | 0.5 | 0.25 |
| 110 | 0.50 | 22.50 | 0.05 | 10 | 45 | 0.98 |
| 169 | 0.50 | 25.00 | 0.05 | 10 | 50 | 0.96 |
| 170 | 0.75 | 24.75 | 0.05 | 15 | 33 | 0.43 |
| 112 | 1.00 | 10.00 | 0.05 | 20 | 10 | 0.36 |
| 171 | 1.00 | 25.00 | 0.05 | 20 | 25 | 0.56 |
| 172 | 1.25 | 25.00 | 0.05 | 25 | 20 | 0.34 |
| 116 | 1.50 | 15.00 | 0.05 | 30 | 10 | 0.28 |
| 173 | 2.00 | 10.00 | 0.05 | 40 | 5 | 0.26 |
| 174 | 3.00 | 7.50 | 0.05 | 60 | 2.5 | 0.21 |
| 175 | 3.00 | 15.00 | 0.05 | 60 | 5 | 0.18 |

Dissolution Test: The CB emulsion was diluted 41 times with PBS.
Phospholipid: EPC:PYL = 7:3 (weight ratio)
Lip/CB: phospholipid (%(w/v))/CB (%(w/v))
L.P./Lip: liquid paraffin (%(w/v))/phospholipid (%(w/v))

Example 12

The same procedures used in Example 9 were repeated except that the liquid paraffin formulation shown in Table 10 was substituted for the liquid paraffin used in the formulation 101 to give CB emulsions. Table 10 shows the formulations of these emulsions and dissolved CB concentrations observed when these emulsions were diluted 41 times with PBS.

The CB emulsions which comprised liquid paraffin products having different specific gravities and viscosities are all excellent in the CB-solubilization ability.

TABLE 10

| Formulation | Phospholipid %(w/v) | Crade of Liquid Paraffin %(w/v) | CB Concn. %(w/v) | Dissolved CB Concn. (μg/ml) |
|---|---|---|---|---|
| 176 | 0.40 | No. 70-S | 18.00 | 0.02 | 0.36 |
| 101 | 0.40 | No. 260-S | 18.00 | 0.02 | 0.46 |
| 177 | 0.40 | No. 350-S | 18.00 | 0.02 | 0.48 |

Dissolution Test: The CE emulsion was diluted 41 times with PBS.
Phospholipid: EPC:PYL = 7:3 (weight ratio)
Liquid Paraffin:
light liquid paraffin No. 70-S [kinematic viscosity 14.10 cst (at 37.8° C.); specific gravity (20/20° C.) 0.841, available from Sanko Chemical Industry Co., Ltd.]
liquid paraffin No. 260-S [kinematic viscosity 56.50 cst (at 37.8° C.); specific gravity (20/20° C.) 0.861, available from Sanko Chemical Industry Co.1 Ltd.]
liquid paraffin No. 350-S [kinematic viscosity 77.00 cst (at 37.8° C.); specific gravity (20/20° C.) 0.876, available from Sanko Chemical Industry Co., Ltd.]

Example 13

The same procedures used in Example 9 were repeated except that phospholipid and an emulsifying agent having the formulation shown in Table 11 were substituted for the phospholipid used in the formulation 100 or 101 to thus give CB emulsions. Table 11 shows the formulations of these emulsions and dissolved CB concentrations observed when these emulsions were diluted 41 times with PBS.

These CB emulsions to which a variety of emulsifying adjuvants were added are all excellent in the CB-solubilization ability.

TABLE 11

| Formulation | Formulation of Phospholipid and Emulsifying Adjuvants %(w/v) | Liquid Paraffin %(w/v) | CB Concn. %(w/v) | Dissolved CB Concn. (μg/ml) |
|---|---|---|---|---|
| 178 | EPC(0.2) | 9.00 | 0.024 | 0.32 |
| 179 | PYL(0.2) | 9.00 | 0.023 | 1.06 |
| 180 | EPC(0.14), PYL(0.06), PCEH(0.02) | 9.00 | 0.02 | 0.88 |
| 181 | EFC(0.28), PYL(0.12), MC(0.012) | 18.00 | 0.02 | 0.38 |
| 182 | EPC(0.28), PYL(0.12), MGL(0.012) | 18.00 | 0.02 | 0.32 |
| 183 | EPC(0.28), PYL(0.12), OA(0.012) | 18.00 | 0.02 | 0.36 |

Dissolution Test: The CB emulsion was diluted 41 times with PBS.
Formulation of Phospholipid-Emulsifying Adjuvants
PCEH: Hydrogenated yolk phosphatidylcholine (available from Nippon Pure Chemical Co., Ltd.)
MC: Dipalmitoyl phosphatidylcholine (MC 6060, available from Nippon Oil and Fats Co., Ltd.)
MGL: Dipalmitoyl phosphatidyl glycerol(MGLS 6060, available from Nippon Oil and Fats Co., Ltd.)
OA: Oleic acid Example 14

The same procedures used in Example 9 were repeated except that α-tocopherol acetate was added to the phospholipid of the formulation 101 to thus give CB emulsions. Separately, the same procedures used in Example 9 were repeated except that α-tocopherol acetate was added to the liquid paraffin of the formulation 101 to thus give CB emulsions.

Table 12 shows the formulations of these emulsions and dissolved CB concentrations observed when these emulsions were diluted 41 times with PBS.

These CB emulsions to which α-tocopherol acetate was added according to different methods are all excellent in the CB-solubilization ability.

TABLE 12

| Formu-lation | Phospholipid Formulation %(w/v) | Oil Formu-lation %(w/v) | CB Concn. %(w/v) | Dissolved CB Concn. (μg/ml) |
|---|---|---|---|---|
| 184 | EPC (0.28), PYL (0.12), toc (0.008) | L.P.(18.00) | 0.02 | 0.48 |
| 185 | EPC (0.28), PYL (0.12) | L.P.(18.00), toc(0.08) | 0.02 | 0.52 |

Dissolution Test: The CB emulsion was diluted 41 times with PBS.
L.P.: liquid paraffin
toc: α-tocopherol acetate Example 15

To a 2% aqueous glycerol solution (pH 6.0) containing 0.5% (w/v) chlorobutanol, 0.01% (w/v) EDTA.2Na, there was added an equal volume of the CB emulsion according to the formulation 100 followed by sufficient mixing. After adjusting the pH of this mixture to 6.0 with HCl, it was filtered through a membrane having a pore size of 0.8 μm to thus prepare a CB emulsion containing the foregoing additives. The resulting emulsion was filled in an eye drop bottle, then thermally sterilized according to the fractional sterilization method to thus give an eye drop of the present invention. The resulting eye drop of the present invention and Ageless (registered trademark) Z (available from Mitsubishi Gas Chemical Co., Inc.) were packaged together in a laminate bag of a polyethylene film and an aluminum foil according to the pillow-packaging technique.

Example 16

To a 2% aqueous glycerol solution (pH 8.0) containing 0.052% (w/v) methyl p-hydroxybenzoate, 0.028% (w/v) propyl p-hydroxybenzoate, 0.1% (w/v) polyvinyl alcohol (degree of polymerization 2000, available from Wako Pure Chemical Co., Ltd.), 0.1% (w/v) histidine and 0.04% (w/v) sodium citrate, there was added an equal volume of the CB emulsion according to the formulation 100 followed by sufficient mixing. After adjusting the pH of this mixture to 8.0 with NaOH, it was filtered through a membrane having a pore size of 0.8 μm to thus prepare a CB emulsion containing the foregoing additives. The resulting emulsion was filled in an eye drop bottle, then thermally sterilized according to the fractional sterilization method to thus give an eye drop of the present invention. Moreover, the resulting eye drop of the present invention and Ageless (registered trademark) Z (available from Mitsubishi Gas Chemical Co., Inc.) were packaged together in a laminate bag of a polyethylene film and an aluminum foil according to the pillow-packaging technique.

Example 17

To a 2% aqueous glycerol solution (pH 7.0) containing 0.052% (w/v) methyl p-hydroxybenzoate, 0.028% (w/v) propyl p-hydroxybenzoate, 0.1% (w/v) polyvinyl pyrrolidone (COLIDONE (registered trademark) 30, available from BASF Aktiengesellschaft) and 0.01% (w/v) EDTA.2Na, there was added an equal volume of the CB emulsion according to the formulation 100 whose pH was adjusted to 7.0 followed by sufficient mixing. The mixture was then filtered through a membrane having a pore size of 0.8 μm to thus prepare a CB emulsion containing the foregoing additives. The resulting emulsion was filled in an eye drop bottle, then thermally sterilized according to the fractional sterilization method to thus give an eye drop of the present invention.

Example 18

The same procedures for preparing emulsions disclosed in Example 1 were repeated except that CP was substituted for FLM to thus prepare CP-containing emulsions according to the present invention. In addition, 50 ml of a 2% aqueous glycerol solution (pH 7.0) was added to 0.05 g of CP, followed by dispersing and suspending the same by stirring and sonication (using BRANSONIC 12 available from Branson Company) and then adjusting the pH thereof to 7.0 with NaOH to thus give a CP-containing suspension.

The following Table 13 shows the formulations of the CP-containing emulsions of the present invention (hereinafter referred to as simply "CP emulsion") and the dissolved CP concentrations observed when these CP emulsions and the foregoing CP-containing suspension as Comparative Example were diluted with PBS.

The CP emulsions of the present invention showed very high dissolved CP concentrations irrespective of the dilution factor with PBS. These results indicate that the emulsion of the present invention which comprises CP, phospholipid, liquid paraffin and water is excellent in solubility of CP in the artificial tear fluid. Incidentally, the following tests of the CP-solubilization ability were carried out at a dilution factor for the CP emulsions of 41 times.

TABLE 13

| Formu-lation | Phospholipid %(w/v) | Liquid Paraffin %(w/v) | CP Concn. %(w/v) |
|---|---|---|---|
| 186 | 0.05 | 2.25 | 0.01 |
| 187 | 0.10 | 5.50 | 0.02 |
| 188 | 0.20 | 10.00 | 0.02 |
| 189 | 0.50 | 5.00 | 0.05 |
| 190 | 0.50 | 25.00 | 0.05 |
| 191 | Suspension | | 0.1 |

| | Dissolved CP Concn. (μg/ml). | | |
|---|---|---|---|
| Formu- | Dilution Factor | | |
| lation | 21 | 41 | 101 |
| 186 | 2.49 | 1.42 | 0.67 |
| 187 | 4.73 | 2.86 | 1.54 |
| 188 | 1.76 | 1.08 | 0.58 |
| 189 | 2.03 | 1.65 | 1.09 |
| 190 | 2.95 | 2.51 | 1.54 |
| 191 | 0.85 | 0.60 | 0.24 |

Dissolution Test: The CP emulsion was diluted from 21 to 101 times with PBS.
Phospholipid: EPC:PYL = 7:3 (weight ratio)
Suspension: 0.1% (w/v) CP, 2% (w/v) glycerol, pH 7.0

Example 19

The same procedures used in Example 18 were repeated except that the CP concentration was variously changed within the range of from 0.0008 to 0.1% (w/v) to give CP emulsions. Table 14 shows the formulations of these CP emulsions and dissolved CP concentrations observed when these emulsions and the suspension as Comparative Example were diluted 41 times with PBS.

Although the dissolved CP concentration increased in proportion to the CP concentration in each CP emulsion, but if it is not less than 0.05% (w/v), the dissolved CP concentration did not increase any more. This clearly indicates that the CP concentration in the CP emulsion is preferably not more than 0.05% (w/v).

TABLE 14

| Formulation | Phospholipid %(w/v) | Liquid Paraffin %(w/v) | CP Concn. %(w/v) | Dissolved CP Concn. (μg/ml) |
|---|---|---|---|---|
| 192 | 0.004 | 0.22 | 0.0008 | 0.11 |
| 193 | 0.0125 | 0.69 | 0.003 | 0.49 |
| 194 | 0.025 | 1.38 | 0.006 | 0.84 |
| 195 | 0.05 | 2.75 | 0.01 | 1.35 |
| 187 | 0.10 | 5.50 | 0.02 | 2.86 |
| 196 | 0.25 | 13.75 | 0.05 | 3.83 |
| 197 | 0.50 | 27.50 | 0.1 | 2.72 |
| 191 | Suspension | | 0.1 | 0.60 |

Dissolution Test: The CP emulsion was diluted 41 times with PBS.
Phospholipid: EPC:PYL = 7:3 (weight ratio)
Suspension: 0.1% (w/v) CP, 2% (w/v) glycerol, pH 7.0

Example 20

The same procedures used in Example 18 were repeated except that the CP, phospholipid and liquid paraffin concentrations were variously changed to give CP emulsions. Table 15 shows the formulations of these emulsions and dissolved CP concentrations observed when these emulsions were diluted 41 times with PBS.

These experiments indicate that the dissolved CP concentration varies depending on the CP concentration in the CP emulsion, the weight ratio of phospholipid to CP and the weight ratio of liquid paraffin to phospholipid. In particular, the CP emulsion excellent in the CP-solubilization ability is those comprising:

A. 0.01 to 0.05% (w/v) of clobetasol propionate;

B. 5 to 10 parts by weight of phospholipid per one part by weight of the component A; and C. 10 to 80 parts by weight of liquid paraffin per one part by weight of the component B.

TABLE 15

| Formulation | Phospholipid %(w/v) | Liquid Paraffin %(w/v) | CP Concn. %(w/v) | Ratio Lip/CP | Ratio L.P./Lip | Dissolved CP, Concn. (μg/ml) |
|---|---|---|---|---|---|---|
| 198 | 0.05 | 0.25 | 0.01 | 5 | 5 | 0.83 |
| 186 | 0.05 | 2.25 | 0.01 | 5 | 45 | 1.42 |
| 195 | 0.05 | 2.75 | 0.01 | 5 | 55 | 1.35 |
| 199 | 0.05 | 4.00 | 0.01 | 5 | 80 | 1.75 |
| 200 | 0.1 | 0.05 | 0.01 | 10 | 0.5 | 0.54 |
| 201 | 0.1 | 5.50 | 0.01 | 10 | 55 | 1.34 |
| 202 | 0.1 | 8.00 | 0.01 | 10 | 80 | 1.57 |
| 203 | 0.3 | 24.00 | 0.01 | 30 | 80 | 0.57 |
| 204 | 0.45 | 24.75 | 0.01 | 45 | 55 | 0.27 |
| 205 | 0.85 | 0.43 | 0.01 | 85 | 0.5 | 0.43 |
| 206 | 0.85 | 25.00 | 0.01 | 85 | 29 | 0.14 |
| 207 | 0.10 | 4.00 | 0.02 | 5 | 40 | 1.43 |
| 187 | 0.10 | 5.50 | 0.02 | 5 | 55 | 2.86 |
| 208 | 0.10 | 8.00 | 0.02 | 5 | 80 | 3.43 |
| 209 | 0.20 | 0.10 | 0.02 | 10 | 0.5 | 1.01 |
| 210 | 0.20 | 0.50 | 0.02 | 10 | 2.5 | 0.91 |
| 188 | 0.20 | 10.00 | 0.02 | 10 | 50 | 1.08 |
| 211 | 0.20 | 16.00 | 0.02 | 10 | 80 | 2.54 |
| 212 | 0.30 | 24.00 | 0.02 | 15 | 80 | 0.98 |
| 213 | 0.40 | 25.00 | 0.02 | 20 | 62.5 | 1.29 |
| 214 | 0.60 | 6.00 | 0.02 | 30 | 10 | 0.58 |
| 215 | 0.60 | 25.00 | 0.02 | 30 | 42 | 0.55 |
| 216 | 0.70 | 22.40 | 0.02 | 35 | 32 | 0.41 |
| 217 | 0.80 | 4.00 | 0.02 | 40 | 5 | 0.55 |
| 218 | 1.20 | 1.20 | 0.02 | 60 | 1 | 0.76 |

TABLE 15-continued

| Formulation | Phospholipid %(w/v) | Liquid Paraffin %(w/v) | CP Concn. %(w/v) | Ratio Lip/CP | Ratio L.P./Lip | Dissolved CP, Concn. (μg/ml) |
|---|---|---|---|---|---|---|
| 219 | 1.20 | 25.00 | 0.02 | 60 | 21 | 0.21 |
| 220 | 1.70 | 0.35 | 0.02 | 85 | 0.2 | 0.33 |
| 221 | 1.70 | 25.00 | 0.02 | 85 | 15 | 0.12 |
| 222 | 0.40 | 22.00 | 0.04 | 10 | 55 | 2.48 |
| 196 | 0.25 | 13.75 | 0.05 | 5 | 55 | 3.83 |
| 223 | 0.25 | 20.00 | 0.05 | 5 | 80 | 3.66 |
| 189 | 0.50 | 5.00 | 0.05 | 10 | 10 | 1.65 |
| 224 | 0.50 | 20.00 | 0.05 | 10 | 40 | 2.12 |
| 190 | 0.50 | 25.00 | 0.05 | 10 | 50 | 2.51 |
| 225 | 0.75 | 25.00 | 0.05 | 15 | 33 | 1.00 |
| 226 | 1.00 | 25.00 | 0.05 | 20 | 28 | 0.40 |
| 227 | 1.25 | 25.00 | 0.05 | 25 | 20 | 0.38 |
| 228 | 1.75 | 0.88 | 0.05 | 35 | 0.5 | 0.97 |
| 229 | 3.00 | 25.00 | 0.05 | 60 | 8.3 | 0.16 |
| 230 | 4.25 | 25.00 | 0.05 | 85 | 5.9 | 0.23 |

Dissolution Test: The CP emulsion was diluted 41 times with PBS.
Phospholipid: EPC:PYL = 7:3 (weight ratio)
Lip/CP: phospholipid (%(w/v))/CP (%(w/v))
L.P./Lip: liquid paraffin (%(w/v))/phospholipid (%(w/v))

Example 21

The same procedures used in Example 18 were repeated except that the liquid paraffin formulation shown in Table 16 was substituted for the liquid paraffin used in the formulation 188 to give CP emulsions. Table 16 shows the formulations of these emulsions and dissolved CP concentrations observed when these emulsions were diluted 41 times with PBS.

The CP emulsions which comprised liquid paraffin products having different specific gravities and viscosities are all excellent in the CP-solubilization ability.

TABLE 16

| Formulation | Phospholipid %(w/v) | Grade of Liquid Paraffin %(w/v) | CP Concn. %(w/v) | Dissolved CP Concn. (μg/ml) |
|---|---|---|---|---|
| 231 | 0.20 | No. 70-5 | 10.00 | 0.02 | 0.92 |
| 232 | 0.20 | No. 150-5 | 10.00 | 0.02 | 1.06 |
| 188 | 0.20 | No. 260-5 | 10.00 | 0.02 | 1.08 |
| 233 | 0.20 | No. 350-5 | 10.00 | 0.02 | 1.17 |

Dissolution Test: The CP emulsion was diluted 41 times with PBS.
Phospholipid: EPC:PYL = 7:3 (weight ratio)
Liquid Paraffin:
light liquid paraffin No. 70-S [kinematic viscosity 14.10 cst (at 37.8° C.); specific gravity (20/20° C.) 0.841, available from Sanko Chemical Industry Co., Ltd.]
liquid paraffin No. 150-S [kinematic viscosity 28.00 cst (at 37.8° C.); specific gravity (20/20° C.) 0.854, available from Sanko Chemical Industry Co., Ltd.]
liquid paraffin No. 260-S [kinematic viscosity 56.50 cst (at 37.8° C.); specific gravity (20/20° C.) 0.861, available from Sanko Chemical Industry Co., Ltd.]
liquid paraffin No. 350-S [kinematic viscosity 77.00 cst (at 37.8° C.); specific gravity (20/20° C.) 0.876, available from Sanko Chemical Industry Co., Ltd.]

Example 22

To a 2% aqueous glycerol solution (pH 6.0) containing 0.5% (w/v) chlorobutanol, 0.01% (w/v) EDTA.2Na, there was added an equal volume of the CP emulsion according to the formulation 222 followed by sufficient mixing of the resulting mixture. After adjusting the pH of this mixture to 6.0 with HCl, it was filtered through a membrane having a pore size of 0.8 μm to thus prepare a CP emulsion containing the foregoing additives. The resulting emulsion was filled in an eye drop bottle, then thermally sterilized according to the fractional sterilization method to thus give an eye drop of the present invention. The resulting eye drop of the present invention and Ageless (registered trademark) Z (available from Mitsubishi Gas Chemical Co., Inc.) were packaged together in a laminate bag of a polyethylene film and an aluminum foil according to the pillow-packaging technique.

Example 23

To a 2% aqueous glycerol solution (pH 8.0) containing 0.052% (w/v) methyl p-hydroxybenzoate, 0.028% (w/v) propyl p-hydroxybenzoate, 0.1% (w/v) polyvinyl alcohol (degree of polymerization 2000, available from Wako Pure Chemical Co., Ltd.), 0.1% (w/v) histidine and 0.04% (w/v) sodium citrate, there was added an equal volume of the CP emulsion according to the formulation 222 followed by sufficient mixing. After adjusting the pH of this mixture to 8.0 with NaOH, it was filtered through a membrane having a pore size of 0.8 μm to thus prepare a CP emulsion containing the foregoing additives. The resulting emulsion was filled in an eye drop bottle, then thermally sterilized according to the fractional sterilization method to thus give an eye drop of the present invention. Moreover, the resulting eye drop of the present invention and Ageless (registered trademark) Z (available from Mitsubishi Gas Chemical Co., Inc.) were packaged together in a laminate bag of a polyethylene film and an aluminum foil according to the pillow-packaging technique.

Example 24

To a 2% aqueous glycerol solution (pH 7.0) containing 0.052% (w/v) methyl p-hydroxybenzoate, 0.028% (w/v) propyl p-hydroxybenzoate, 0.1% (w/v) polyvinyl pyrrolidone (COLIDONE (registered trademark) 30, available from BASF Aktiengesellschaft) and 0.01% (w/v) EDTA.2Na, there was added an equal volume of the CP emulsion according to the formulation 222 whose pH was adjusted to 7.0 followed by sufficient mixing of the resulting mixture. The mixture was then filtered through a membrane having a pore size of 0.8 μm to thus prepare a CP emulsion containing the foregoing additives. The resulting emulsion was filled in an eye drop bottle, then thermally sterilized according to the fractional sterilization method to thus give an eye drop of the present invention.

TEST EXAMPLES

Test Example 1

Test for Determining Distribution of FLM in Conjunctiva After Instillation of FLM Emulsion Eye Drop in the Eyes (Methodology) The fluorometholone-containing O/W emulsion eye drop prepared in Example 8 according to the present invention or the formulation 5 (an FLM-containing suspension; Flumetholon 0.1) (50 μl each) was instilled in the eyes of arbino rabbits, followed by determining the FLM concentrations in the conjunctiva observed at 5, 15 and 60 minutes after the instillation thereof in the eyes. The FLM concentrations in the conjunctiva were quantitatively determined by homogenizing the conjunctiva, extracting the homogenate with an organic solvent, distilling off the organic solvent in the extract, then dissolving the resulting residue in a moving phase for HPLC and subjecting it to HPLC under the following conditions.

HPLC Conditions:

Column: ChemcoPak (Chemcosorb 5-ODS-H, available from Chemco Company);

Moving Phase: 35% (v/v) acetonitrile/water;

Flow Rate: 0.7 ml/min;

Detection: UV light rays of 240 nm.

Figure 1:
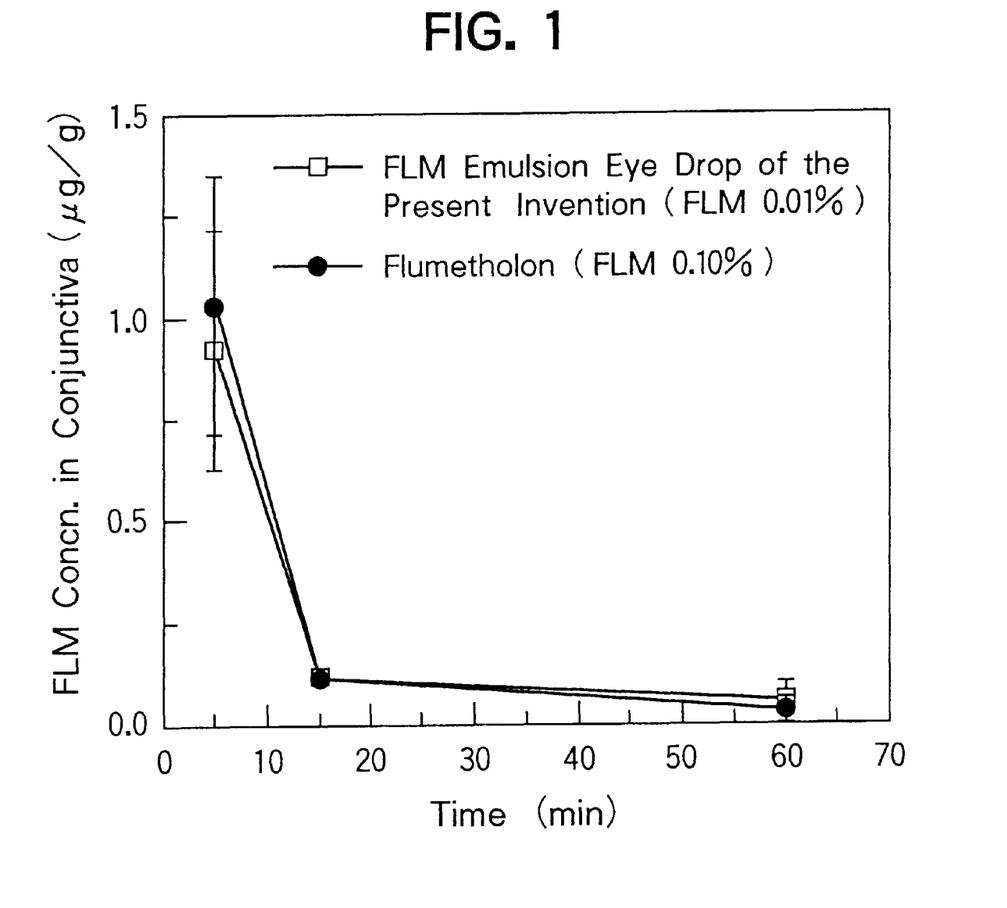
FIG. 1 is a graph showing the fluorometholone (FLM) concentrations in the conjunctiva of an arbino rabbit observed after instillation, in the eyes thereof, an FLM-containing emulsion eye drop and a pharmaceutical preparation containing suspended FLM (average value±S.D.; n=3 to 4).

(Experimental Results) The following Table 17 and FIG. 1 show the formulations of the eye drops used in these experiments, the FLM concentration dissolved in PBS and the FLM concentrations in the conjunctiva at 5, 15 and 60 minutes after the dropping these eye drops in the eyes. Although the FLM concentration in the FLM emulsion eye drop of the present invention was about 1/10 time that in the suspension, there was not observed any difference in the concentration of the drug in the conjunctiva.

TABLE 17

| Eye Drop | Phospholipid %(w/v) | Liquid Paraffin %(w/v) | FLM Concn. %(w/v) | Dissolved FLM Concn. (μg/ml) |
|---|---|---|---|---|
| FLM Emulsion Eye Drop of Example 8 | 0.42 | 4.2 | 0.01 | 1.5 |
| Suspension having Formulation 5 (Flumetholon 0.1) | — | — | 0.10 | 1.5 |

| | FLM Concn. in Conjunctiva: ~g/g(S.D.) | | |
|---|---|---|---|
| | Time Elapsed after Dropping in the Eyes (min) | | |
| Eye Drop | 5 | 15 | 60 |
| FLM Emulsion Eye Drop of Example 8 | 0.924(±0.293) | 0.123(±0.002) | 0.052(±0.053) |
| Suspension having Formulation 5 (Flumetholon 0.1) | 1.031(±0.318) | 0.116(±0.027) | 0.035(±0.030) |

Dissolution Test: The FLM emulsion was diluted 51 times with PBS.
The FLM concentrations in the conjunctiva each is the average of three to four measurements.

Test Example 2

Test for Determining Distribution of CB in Ocular Tissues After Instillation of CB Emulsion Eye Drop in the Eyes (Preparation of Sample) There was prepared a CB emulsion containing 0.04% (w/v) CB, 0.4% (w/v) phospholipid [EPC:PYL=7:3 (weight ratio)], 20% (w/v) liquid paraffin and 2% (w/v) glycerol by the same method disclosed in Example 9. To the resulting emulsion, there was added an equal volume of a 2% aqueous glycerol solution (pH 7.0) containing 0.052% (w/v) methyl p-hydroxybenzoate, 0.028% (w/v) propyl p-hydroxybenzoate and 0.01% (w/v) EDTA.2Na followed by sufficient mixing thereof. After adjusting the pH of the mixture to 7.0 with NaOH, the solution was filtered through a membrane having a pore size of 0.8 μm and then filled in an eye drop bottle. Thereafter it was thermally sterilized by the fractional sterilization technique to thus give a CB emulsion eye drop according to the present invention.

(Methodology) The CB emulsion eye drop prepared above according to the present invention or a CB-containing suspension according to the formulation 103 [CLOBURATE (registered trademark), 0.1% (w/v) CB, available from Cusi (UK) Ltd.] (50 μl each) was instilled in the eyes of arbino rabbits, followed by determining the CB concentrations in ocular tissues (the conjunctiva, cornea and aqueous humor)

observed at 5, 30 and 120 minutes after the eye drops. The CB concentrations in the ocular tissues were quantitatively determined by homogenizing each corresponding tissue, extracting the resulting homogenate with an organic solvent, distilling off the organic solvent in the extract, then dissolving the resulting residue in a moving phase for HPLC and subjecting it to HPLC under the following conditions.

HPLC Conditions:

Column: YMC-Pack ODS-AQ (AQ-312) (available from YMC Company);

Moving Phase: 67% (v/v) acetonitrile/50 mM phosphate buffer (pH 6.0);

Flow Rate: 1.0 ml/min;

Detection: UV light rays of 245 nm.

Figure 2:
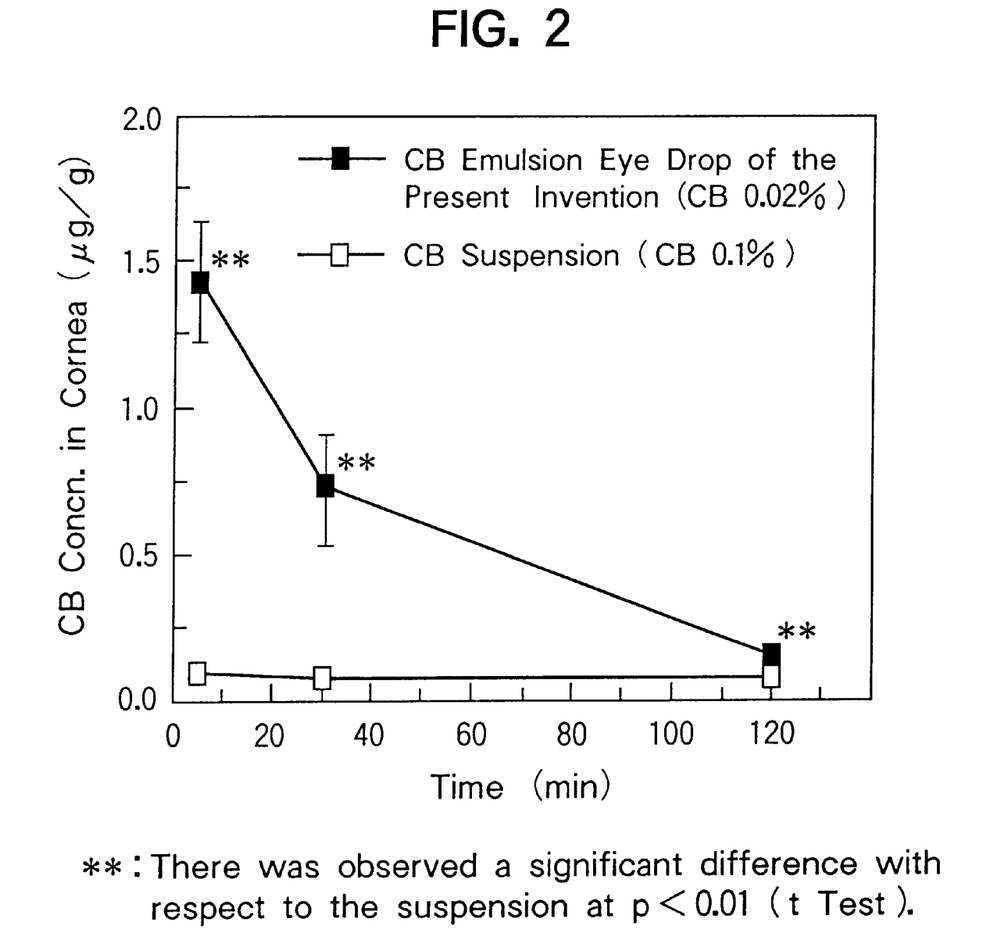
FIG. 2 is a graph showing the clobetasone butyrate (CB) concentrations in the cornea of an arbino rabbit observed after instillation, in the eyes thereof, a CB-containing emulsion eye drop and a pharmaceutical preparation containing suspended CB (average value±S.D.; n=4).

(Experimental Results) The following Table 18 and FIG. 2 show the formulations of the eye drops used in these experiments, the CB concentration dissolved in PBS and the CB concentrations in the ocular tissues at 5, 30 and 120 minutes after the instillation of these eye drops in the eyes. Although the CB concentration in the CB emulsion eye drop of the present invention was about ⅕ time that in the suspension, there was difference in the CB concentrations in the tissues between the emulsion eye drop according to the present invention and the comparative suspension.

TABLE 18

| Eye Drop | Phospholipid %(w/v) | Liquid Paraffin %(w/v) | CB Concn. %(w/v) | Dissolved CB Concn. (μg/ml) |
|---|---|---|---|---|
| CB Emulsion Eye Drop | 0.2 | 10 | 0.02 | 0.67 |
| Suspension having Formulation 103 (CLOBURATE) | — | — | 0.1 | 0.17 |

Dissolution Test: The CP emulsion was diluted 41 times with PBS.
Phospholipid: EPC:PYL = 7:3 (weight ratio)
Additives Included in the CB Emulsion Eye Drop:

| methyl p-hydroxybenzoate | 0.026% (w/v) |
| propyl p-hydroxybenzoate | 0.014% (w/v) |
| disodium ethylenediaminetetraacetate | 0.005% (w/v) |
| glycerol | 2% (w/v) |

| | Time Elapsed after Dropping in the Eyes(min) | | |
|---|---|---|---|
| Eye Drop | 5 | 30 | 120 |
| CB Concn. in Conjunctiva: μg/g (S.D.) | | | |
| CB Emulsion Eye Drop | 0.98(±0.14)** | 0.20(±0.08)* | 0.00 |
| Suspension having Formulation 103 (CLOBURATE) | 0.10(±0.07) | 0.07(±0.06) | 0.12(±0.11) |
| CB Concn. in Cornea: μg/g (S.D.) | | | |
| CB Emulsion Eye Drop | 1.43(±0.21)** | 0.71(±0.19)** | 0.14(±0.03) |
| Suspension having Formulation 103 (CLOBURATE) | 0.09(±0.03) | 0.07(±0.02) | 0.07(±0.03) |
| CB Concn. in Aqueous Humor: ng/ml (S.D.) | | | |
| CB Emulsion Eye Drop | 0.00 | 4.57(±1.78)** | 4.60(±1.19) |
| Suspension having Formulation 103 (CLOBURATE) | 0.00 | 0.38(±0.75) | 1.17(±1.13) |

TABLE 18-continued

*Each eye drop was dropped in the eyes of arbino rabbits i n an amount of 50 μl each.
*The CB concentrations in the ocular tissues (conjunctiva, cornea and aqueous humor) each is the average of three to four measurements.
*: There was observed a significant difference with respect to the suspension at p < 0.05 (t Test).
**: There was observed a significant difference with respect to the suspension at p < 0.01 (t Test).

INDUSTRIAL APPLICABILITY

The O/W emulsion composition for eye drops according to the present invention has been proved to be excellent in solubility of fluorometholone, clobetasone butyrate and clobetasol propionate in the tear fluid. Therefore, the composition would exhibit an anti-inflammatory activity identical to or superior to those achieved by the fluorometholone aqueous suspension (commercially available pharmaceutical preparation), the clobetasone butyrate aqueous suspension (commercially available pharmaceutical preparation) and the clobetasol propionate aqueous suspension, by the administration thereof at a dose lower than those required for these commercial drugs. The composition would also be excellent from the economical standpoint and permit reduction of systemic side effects which would be encountered when the conventional drugs are dropped in the eyes.

What is claimed is:

1. An O/W emulsion composition for eye drops, consist essentially of a drug selected from the group consisting of fluorometholone, clobetasone butyrate and clobetasol propionate; a phospholipid; liquid paraffin; and water.

2. The O/W emulsion composition of claim 1 which consist essentially of the following components A to D:
   A. a drug selected from the group consisting of fluorometholone, clobetasone butyrate and clobetasol propionate in an amount ranging from 0.001 to 0.05% (w/v);
   B. a phospholipid in an amount ranging from 5 to 240 parts by weight per one part by weight of the component A;
   C. liquid paraffin in an amount ranging from 0.5 to 80 parts by weight per one part by weight of the component B and at a concentration in the O/W emulsion of not more than 25% (w/v); and
   D. water in a suitable amount.

3. The O/W emulsion composition of claim 1 which consist essentially of the following components A to D:
   A. fluorometholone in an amount ranging from 0.001 to 0.05% (w/v);
   B. a phospholipid in an amount ranging from 10 to 240 parts by weight per one part by weight of the component A;
   C. liquid paraffin in an amount ranging from 0.5 to 20 parts by weight per one part by weight of the component B and at a concentration in the O/W emulsion of not more than 25% (w/v); and
   D. water in a suitable amount.

4. The O/W emulsion composition of claim 3, which consist essentially fluorometholone in an amount ranging from 0.005 to 0.05% (w/v).

5. The O/W emulsion composition of claim 1, which consist essentially of the following components A to D:
   A. clobetasone butyrate or clobetasol propionate in an amount ranging from 0.001 to 0.05% (w/v);
   B. a phospholipid in an amount ranging from 5 to 85 parts by weight per one part by weight of the component A;

C. liquid paraffin in an amount ranging from 0.5 to 80 parts by weight per one part by weight of the component B and at a concentration in the O/W emulsion of not more than 25% (w/v); and D. water in a suitable amount.

6. The O/W emulsion composition of claim 5, which consist essentially of the following components A to D:

A. clobetasone butyrate in an amount ranging from 0.006 to 0.05% (w/v);

B. a phospholipid in an amount ranging from 10 to 25 parts by weight per one part by weight of the component A;

C. liquid paraffin in an amount ranging from 5 to 80 parts by weight per one part by weight of the component B and at a concentration in the O/W emulsion of not more than 25% (w/v); and D. water in a suitable amount.

7. The 0/W emulsion composition of claim 5, which consist essentially of the following components A to D:

A. clobetasol propionate in an amount ranging from 0.01 to 0.05% (w/v);

B. a phospholipid in an amount ranging from 5 to 10 parts by weight per one part by weight of the component A;

C. liquid paraffin in an amount ranging from 10 to 80 parts by weight per one part by weight of the component B and at a concentration in the O/W emulsion of not more than 25% (w/v); and D. water in a suitable amount.

8. The O/W emulsion composition of claim 1, which consist essentially of an isotonizing agent or a preservative or a mixture thereof.

9. The O/W emulsion composition of claim 1, which consist essentially of, as a stabilizer, at least one member selected from the group consisting of tocopherol and compounds thereof, amino acids, citric acid, EDTA and pharmaceutically acceptable salts thereof.

10. The O/W emulsion composition of claim 1, wherein the phospholipid is selected from the group consisting of yolk lecithin, soybean lecithin and lyso-forms and hydrogenated products thereof.

11. The O/W emulsion composition of claim 1, wherein the phospholipid is selected from the group consisting of phosphatidylcholine, phosphatidylethanolamine, phosphatidyl serine, phosphatidylinositol, phosphatidylglycerol, dicetyl phosphate, sphingomyelin, dimyristoyl phosphatidyl choline, dipalmitoyl phosphatidylcholine and distearoyl phosphatidyl choline.

12. The O/W emulsion composition of claim 1, wherein said liquid paraffin has a specific gravity (20/20° C.) of from 0.830 to 0.870 and a kinematic viscosity (as determined at 37.8° C.) of less than 37 cst.

13. The O/W emulsion composition of claim 1, wherein said liquid paraffin has a specific gravity (20/20° C.) of from 0.860 to 0.890 and a kinematic viscosity (as determined at 37.8° C.) of not less than 37 cst.

14. The O/W emulsion composition of claim 9, wherein said tocopherol compound is selected from the group consisting of tocopherol acetate, tocopherol nicotinate and tocopherol succinate.

15. The O/W emulsion composition of claim 1, which has a pH of from 4.5 to 8.5.

16. The O/W emulsion composition of claim 15, which has a pH of from 6.0 to 8.0.

17. The O/W emulsion composition of claim 1, wherein the phospholipid is selected from the group consisting of yolk lecithin, soybean lecithin, lyso-forms and hydrogenated products of yolk lecithin and soybean lecithin, phosphatidylcholine, phosphatidylethanolanine, phosphatidylserine, phosphatidylinositol, phosphatidylglycerol, dicetyl phosphate, sphingomyelin, dimyristoyl phosphatidylcholine, dipalmitoyl phosphatidylcholine, and distearoyl phosphatidylcholine.

18. The O/W emulsion composition of claim 1, wherein the liquid paraffin has a specific gravity (20/20° C.) ranging from 0.830 to 0.860, and a kinematic viscosity (as determined at 37.8° C.) of less than 37 cst.

19. The O/W emulsion composition of claim 1, wherein the liquid paraffin has a specific gravity (20/20° C.) ranging from 0.860 to 0.890, and a kinematic viscosity (as determined at 37.8° C.) of not less than 37 cst.

20. The O/W emulsion composition of claim 1, which has a pH ranging from 4.5 to 8.5.

21. The O/W emulsion composition of claim 20, which has a pH ranging from 6.0 to 8.0.

* * * * *